(12) United States Patent
Bue, Jr. et al.

(10) Patent No.: US 9,357,804 B2
(45) Date of Patent: Jun. 7, 2016

(54) PROPRIOCEPTIVE TOPICAL ANKLE GEAR AND METHODS OF USE

(75) Inventors: William D. Bue, Jr., Austin, TX (US); Michael L. Martin, Bainbridge Island, WA (US); Elizabeth Danflous Russell, Austin, TX (US)

(73) Assignee: Topical Gear, LLC, Austin, TX (US)

( * ) Notice: Subject to any disclaimer, the term of this patent is extended or adjusted under 35 U.S.C. 154(b) by 327 days.

(21) Appl. No.: 13/884,492

(22) PCT Filed: Nov. 14, 2011

(86) PCT No.: PCT/US2011/060593
§ 371 (c)(1),
(2), (4) Date: Aug. 20, 2013

(87) PCT Pub. No.: WO2012/065165
PCT Pub. Date: May 18, 2012

(65) Prior Publication Data
US 2013/0326799 A1    Dec. 12, 2013

Related U.S. Application Data

(60) Provisional application No. 61/413,056, filed on Nov. 12, 2010, provisional application No. 61/705,134, filed on Sep. 24, 2012.

(51) Int. Cl.
*A61F 5/00* (2006.01)
*A41D 13/05* (2006.01)
*A61F 5/01* (2006.01)

(52) U.S. Cl.
CPC .............. *A41D 13/05* (2013.01); *A61F 5/0111* (2013.01)

(58) Field of Classification Search
CPC ..... A61F 5/0111; A61F 13/08; A61F 5/0127; A61F 2002/0086; A61F 2005/0137; A61F 2205/0068; A61F 2/08; A61F 5/24; A61F 7/00; A61F 7/03; A61F 7/106; A61F 13/00025; A61F 13/00034; A61F 13/00059; A61F 13/00063; A61F 13/00068; A61F 13/02; A61F 13/066; A61F 13/068; A61F 13/10; A61F 13/101; A43B 5/10; A43B 7/20; A43B 23/17; A43B 13/223; A43B 5/06; A41D 13/05; A61H 1/006; A61H 2201/164; A61H 2201/165; A61H 39/04; A63B 2071/1258; A63B 2209/10
USPC ................................................ 602/23, 26, 27
See application file for complete search history.

(56) References Cited

U.S. PATENT DOCUMENTS 958,199 A * 5/1910 Ward ............................ 128/894
4,323,058 A  4/1982 Detty
(Continued)

OTHER PUBLICATIONS

International Search Report for PCT/US2011/060593 dated Mar. 26, 2012.
(Continued)

*Primary Examiner* — Michael Brown
(74) *Attorney, Agent, or Firm* — Rodney J. Fuller; Booth Udall Fuller, PLC

(57) ABSTRACT

The present invention is directed to topical ankle gear for enhancing performance and reducing the risk of injury. The topical ankle gear and kits preferably comprise a flexible sleeve and a lateral foot-ankle buttress, Achilles buttresses, and/or an extendable strap. The topical ankle gear of the present invention is designed to be worn during periods of physical activity to reduce injury and to train and strengthen the athletes muscles against injury, advantageously increasing proprioception by stimulating critical sensory and tactile receptors in the foot and ankle.

18 Claims, 5 Drawing Sheets

(56) References Cited

U.S. PATENT DOCUMENTS

| | | |
|---|---|---|
| 4,556,054 A | 12/1985 | Paulseth |
| 4,702,234 A | 10/1987 | Huntjens |
| 4,841,957 A * | 6/1989 | Wooten et al. .................. 602/27 |
| 5,135,473 A | 8/1992 | Epler et al. |
| 5,599,610 A | 2/1997 | Levy |
| 5,810,754 A * | 9/1998 | Kenosh ........................... 602/27 |
| 6,083,184 A | 7/2000 | Kenosh |
| 6,558,339 B1 * | 5/2003 | Graham .......................... 602/66 |
| 6,929,617 B2 | 8/2005 | McCormick et al. |
| 8,251,932 B2 * | 8/2012 | Fout ...................... A61F 5/0111 36/169 |
| 2010/0016813 A1 * | 1/2010 | Brown et al. ................. 604/293 |

OTHER PUBLICATIONS

Written Opinion of the International Searching Authority for PCT/US2011/060593 dated Mar. 26, 2012.

International Preliminary Report on Patentability for PCT/US2011/060593 dated Nov. 16, 2012.

* cited by examiner

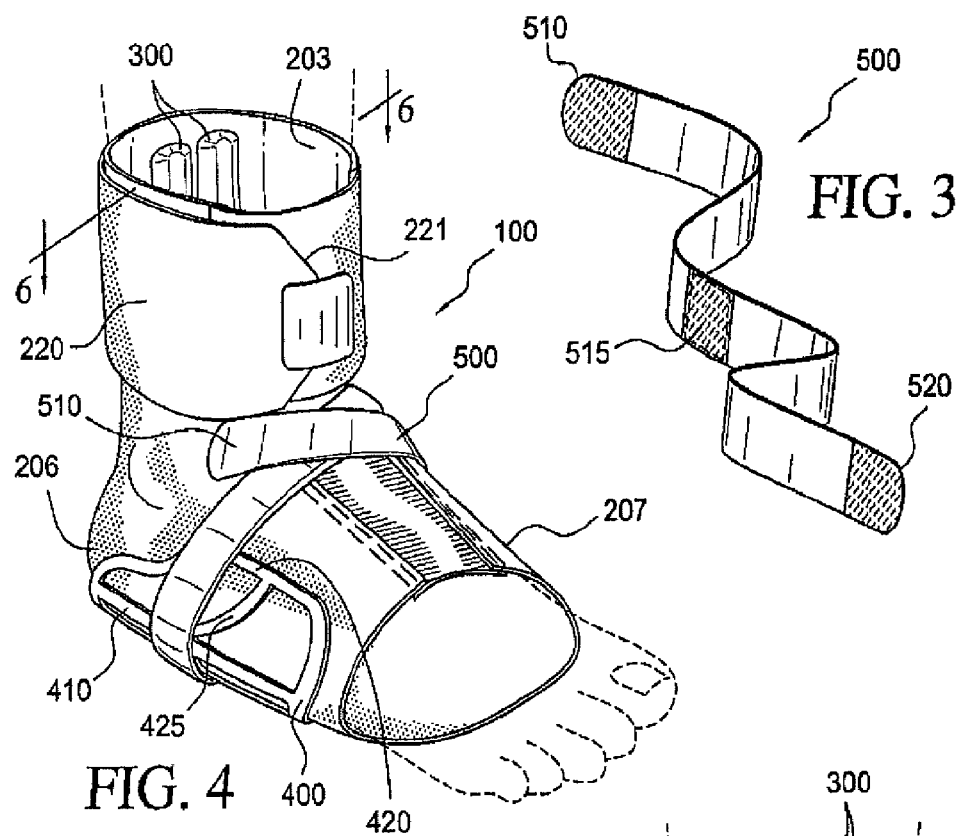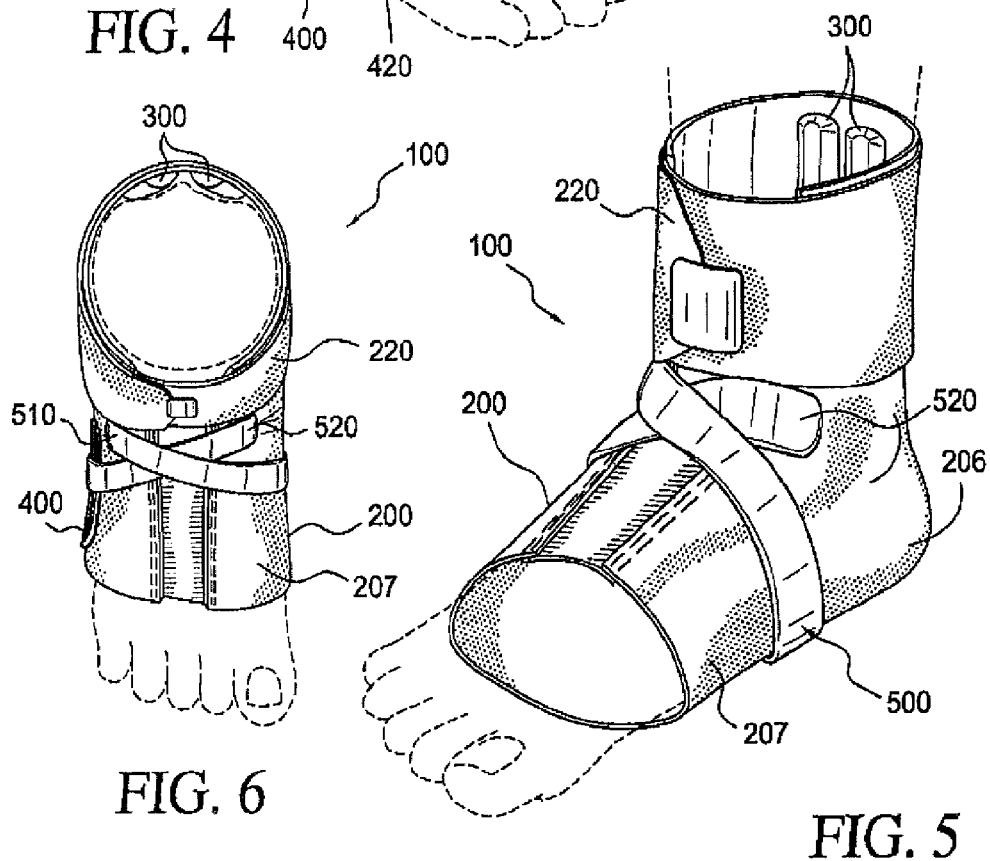

PROPRIOCEPTIVE TOPICAL ANKLE GEAR AND METHODS OF USE

CROSS REFERENCE TO RELATED APPLICATIONS

This application is the U.S. National Stage of PCT/US2011/060593, filed Nov. 14, 2011, which claims the benefit of U.S. Provisional Application No. 61/413,056, filed Nov. 12, 2010 and also claims the benefit of U.S. Provisional Application No. 61/705,134, filed Sep. 24, 2012, the content of each of which is expressly incorporated herein in its entirety by reference thereto.

BACKGROUND OF THE INVENTION

1. Field of the Invention

The present invention is directed to topical ankle gear for enhancing performance and reducing the risk of injury. The topical ankle gear preferably comprises a flexible sleeve with a lateral foot-ankle buttress, Achilles buttresses, and/or an extendable strap. It is designed to be worn during periods of physical activity. In a preferred embodiment, each component of the topical ankle gear is non-rigid or semi-rigid, and the invention increases proprioception by stimulating critical sensory and tactile receptors in the foot and ankle.

2. Discussion of the Background

Ankle braces have long been a fixture in the realm of sports medicine and athletic training. For decades, the ankle brace market has relied on bulky, rigid designs and taping. Indeed, current ankle braces trace their origins to stirrup-based designs patented in the 1890's. See, e.g. U.S. Pat. No. 29,415 (filed Aug. 31, 1898). Other designs resemble a standard tape job frequently applied to an athlete by an athletic trainer. Such braces rely on outmoded technology and fail to address the latest in neuromuscular research. Moreover, although some of these braces purportedly prevent injury, most are designed for application post-injury, as a means of treating foot and ankle injuries after the fact. A growing number of experts (including those with the most practical experience with ankle braces, such as athletic trainers and coaches) are recognizing the shortcomings of the current crop of ankle braces: typically making the ankle weaker, transferring load up the limb, and restricting range of motion of the ankle and foot. The prior art ankle braces were not designed to strengthen and condition the ankle naturally. As a result, a need exists for topical ankle gear that will proactively strengthen the ankle and reduce the risk of injury.

SUMMARY OF THE INVENTION

The topical ankle gear of the present invention addresses the long-felt need described above. Instead of a rigid, restrictive brace, the present invention combines a flexible sleeve with a semi-rigid lateral buttress and compressible Achilles buttresses (all of which are preferably further secured by an extendable strap affixed with hook-loop fasteners) to proactively strengthen the ankle and reduce the risk of injury. The invention applies topical pressure to select areas of the foot and ankle, thereby stimulating critical neuroreceptors and improving the user's proprioception, motor skills, Hoffman reflex ("H-reflex"), and overall flexibility.

The form of the topical ankle gear follows its function. For example, the taco-shaped lateral buttress places topical pressure on tactile receptors in the anterior talofibular ligament (ATFL) and calcaneo fibular ligaments in order to stimulate the stretch reflex, thereby reducing the latency period in the attached muscle spindles. This semi-rigid lateral buttress fits (simultaneously) under, around, and on top of the foot. So positioned, the buttress stimulates the tactile receptors and provides resistance during the plantar flexion and inversion moments. Research indicates that an athlete receives maximum proprioceptive stimulation from a semi-rigid material (like the material comprising the lateral, taco-shaped buttress).

In addition, the present invention includes compressible Achilles buttresses that apply pressure to the peroneal muscle group. This region of the ankle is particularly rich in sensory and tactile receptors, including the golgi tendon origin. The Achilles buttresses stimulate the peroneus longus (PL), peroneus brevis (PB), and tibialis anterior (TA) muscle spindles, which collectively comprise the body's primary defense against the inversion moment. Overall, the topical gear of the present invention enhances neuromuscular communication, which shortens the stretch reflex in the muscle spindles and reduces the load on the ligaments. In so doing, the present invention proactively reduces the risk of injury.

Unlike the bulky, strap-heavy, rigid braces currently on the market, the topical gear of the present invention fits snugly and comfortably over the foot, ankle, and lower leg of the user without substantially reducing his or her range of motion. The present invention is up to 60% lighter and up to 50% less bulky than typical existing ankle braces. It is designed to protect a user's ATFL, and does not transfer load up the limb like most existing braces. In addition, the topical gear described herein preserves the full range of motion in the foot and ankle. This helps to maintain healthy joints and connective tissue. Thus, instead of weakening the ankle, the present invention strengthens the ankle and reduces fatigue—which studies have shown is a leading cause of injury in the foot and ankle. As an added benefit, the topical gear takes only seconds to apply and, unlike existing braces, can be worn during physical rehabilitation, strength and conditioning, practice, and games.

BRIEF DESCRIPTION OF THE DRAWINGS

The accompanying drawings, described below, illustrate preferred embodiments of the present invention. These drawings depict various features and further advantages of the present invention. Reference numbers indicate identical or functionally similar elements. It will be understood that no limitation to the scope of the invention is intended thereby. These drawings depict various features and further advantages of the present invention. The invention is not limited to the particular embodiments disclosed in these drawings, as it should be understood by one skilled in the art that additional features, modifications, and alternative embodiments are contemplated by the invention as disclosed herein.

FIG. 3 is a perspective view of an extendable strap for a preferred embodiment of the present invention.

FIG. 4 is a front and right-side perspective view of a preferred embodiment of the present invention showing the extendable strap in a "figure-eight" configuration.

FIG. 5 is a front and left-side perspective view of a preferred embodiment of the present invention showing the extendable strap in a "figure-eight" configuration.

FIG. 6 is a top-plan view of a preferred embodiment of the present invention showing the extendable strap in a "figure-eight" configuration.

DETAILED DESCRIPTION OF THE PREFERRED EMBODIMENTS

The following is a description of the preferred embodiments of the present invention and is not intended to limit the scope of the invention to the particular embodiments discussed below.

Figure 1:
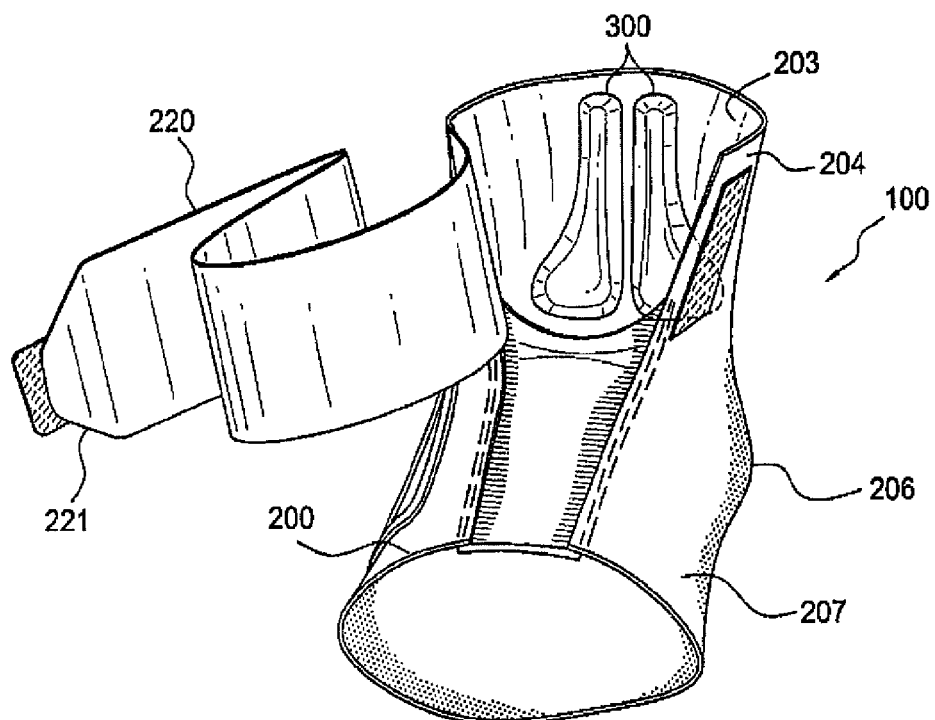
FIG. 1 is a front perspective view of a preferred embodiment of the present invention.
Figure 2:
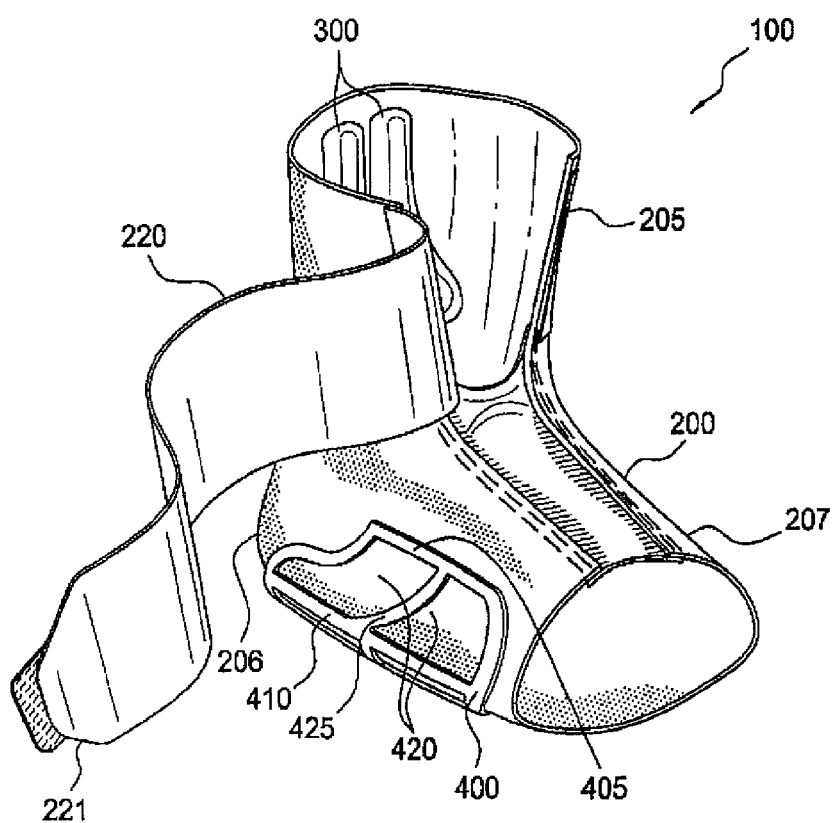
FIG. 2 is a front and right-side perspective view of a preferred embodiment of the present invention.
Figure 7:
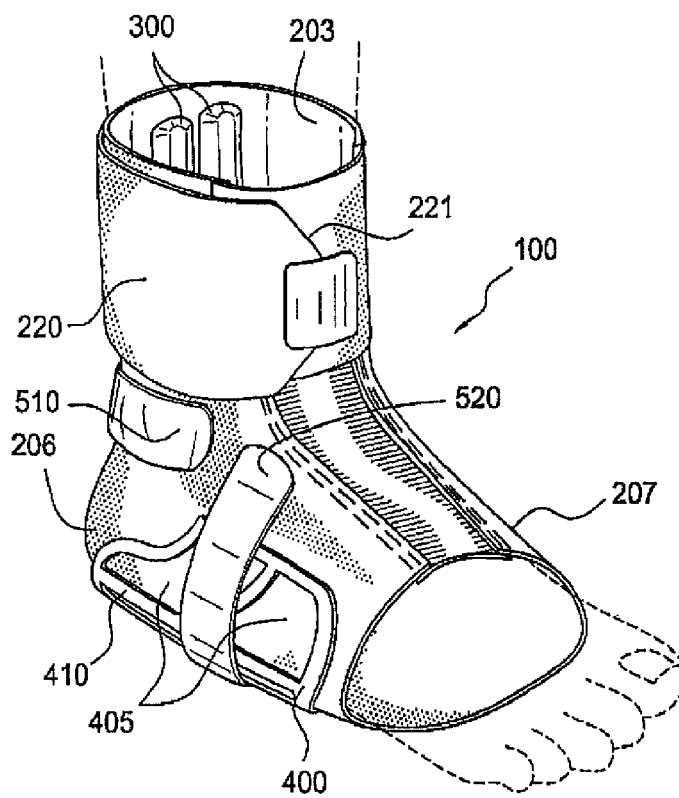
FIG. 7 is a front and right-side perspective view of a preferred embodiment of the present invention showing the extendable strap in a "heel-lock" configuration.
Figure 8:
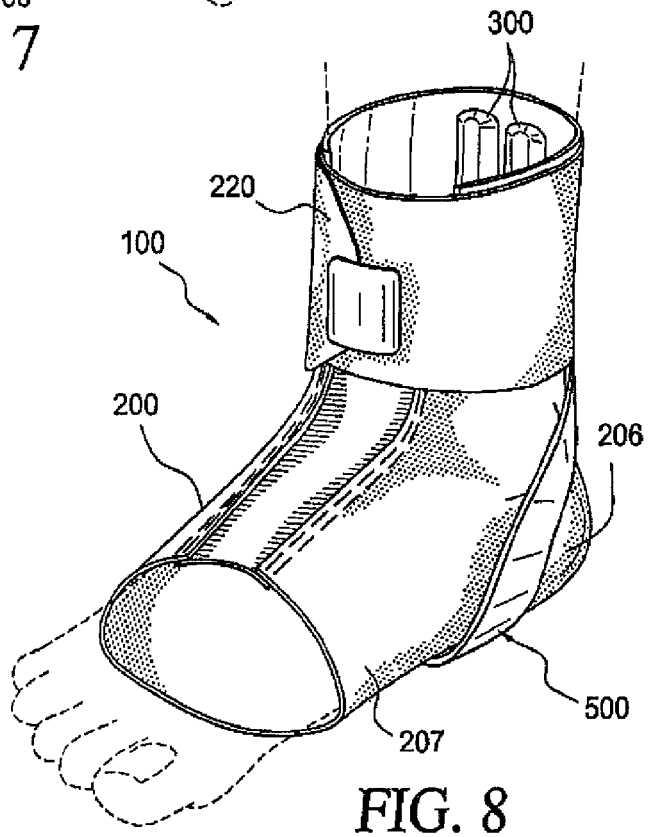
FIG. 8 is a front and left-side perspective view of the present invention showing the extendable strap in a "heel-lock" configuration.

In accordance with the present invention, FIGS. 1-2 depict topical ankle gear 100 for enhancing performance and reducing the risk of injury. In a preferred embodiment, the topical ankle gear 100 includes flexible sleeve 200, which is comprised of lower leg encircling portion 205, ankle encircling portion 206, and foot encircling portion 207. Both interior surface 203 and exterior surface 204 of flexible sleeve 200 are shown. Flexible sleeve 200 is comprised of a thin, resilient, radially stretchable material designed to conform and contour to a user's lower leg, ankle, and foot. Preferably, flexible sleeve 200 is comprised of a loose-knit fiber breathably configured to release perspiration and allow air flow during use. The loose-knit fiber can be any one of a number of commercially available stretchable materials such as LYCRA, SPANDEX, BIOSKIN, or EpX. More preferably, the material is a tri-laminate (bonded) material having a first polyurethane-polyurea copolymer on the inside and a second polyurethane-polyurea copolymer on the outside, with a thin polyurethane membrane between the first and second copolymers. In a preferred embodiment, the tri-laminate material is less than 2 mm thick and is sufficiently elastic to provide between 15-25 mm Hg compression to the lower leg, ankle, and/or foot of the user.

In a preferred embodiment, the lower leg encircling portion 205 and least a portion of the ankle encircling portion 206 (preferably just above the heel) of the flexible sleeve 200 has at least a 10% to 15% reduced diameter compared to the foot encircling portion 207, more preferably at least a 20% to 25% reduced diameter, and most preferably at least a 30% reduced diameter compared to the foot encircling portion 207 of the flexible sleeve 200. This embodiment has been found to be most beneficial to certain athletes.

As shown in FIGS. 1-2, flexible sleeve 200 further comprises strap 220 extending therefrom and configured to extend substantially circumferentially around and couple to lower leg encircling portion 205 at distal end 221. Preferably, strap 220 further comprises one or more hook loop fasteners affixed to a portion of distal end 221, wherein the hook loop fasteners are suitable for releasably coupling distal end 221 to lower leg encircling portion 205 when topical ankle gear 100 is worn by a user. FIGS. 1-2 depict strap 220 in an unaffixed (open) position, whereas FIGS. 4-8 show strap 220 with distal end 221 affixed to lower leg encircling portion 205.

Advantageously, topical ankle gear 100 further comprises one or more Achilles buttresses 300. FIG. 1 provides a front elevational view of a preferred embodiment of Achilles buttresses 300, and FIGS. 2, 4-5, and 7-8 show various (partial) views of the same. FIG. 6 provides a top-plan view of a preferred embodiment of Achilles buttresses 300. Preferably, ankle gear 100 includes a first and second Achilles buttress 300 coupled to the interior surface 203 of flexible sleeve 200 and extending vertically thereabove along the interior of lower leg encircling portion 205 as shown in FIG. 1. More preferably, Achilles buttresses 300 are positioned such that when the topical ankle gear 100 is worn by a user, the first and second Achilles buttresses are in contact with the Achilles tendon of the user. Most preferably, the Achilles buttresses 300 are positioned such that the first Achilles buttress extends vertically along one side of the Achilles tendon and the second Achilles buttress extends vertically along the opposing side of the Achilles tendon. In their preferred embodiment, Achilles buttresses 300 are substantially elliptical and are comprised of a compressible material. Flexible sleeve 200 compresses first and second Achilles buttresses 300 toward the user's Achilles tendon with a force sufficient to stimulate sensory and tactile receptors in the foot and ankle. Preferably, the compressible material is comprised of one or more of the following: a foam or foam-like material, a gel or gel-like material, or any other compressible material suitable to conform to the Achilles tendon and apply pressure to one or more constituents of the peroneal muscle group. Most preferably, the Achilles buttresses 300 stimulate the peroneus longus (PL), peroneous brevis (PB), and/or tibialis anterior (TA) muscle spindles.

In a preferred embodiment, ankle gear 100 further includes lateral foot-ankle buttress 400, which is comprised of flared upper portion 405, medial portion 410, and flared lower portion 415. Lateral foot-ankle buttress 400 preferably couples to the foot encircling portion 207 of flexible sleeve 200 and extends into the ankle portion 206 thereof. So positioned, flared upper portion 405 extends over and provides resistance to an anterior (top) portion of the foot of a user. Preferably, flared upper portion 405 is further configured to fit under—and in close proximity to—a user's malleolus. The medial portion 410 of lateral foot-ankle buttress 400 is configured to conform to and extend around a user's foot, thereby providing resistance to a lateral portion of the foot, whereas the flared lower portion 415 is configured to extend under and provide resistance to a posterior portion of the foot (the sole of the foot).

In this preferred placement, lateral foot-ankle buttress 400 will advantageously stimulate the sensory and tactile receptors of a user's foot and ankle when worn. Preferably, taco-shaped lateral buttress 400, when properly positioned, places topical pressure on tactile receptors in the anterior talofibular ligament (ATFL) and calcaneo fibular ligaments. More preferably, taco-shaped lateral buttress 400 will stimulate the stretch reflex, thereby reducing the latency period in the attached muscle spindles by at least one millisecond. After extended use (1-2 weeks) taco-shaped lateral buttress 400 reduces the latency period by up to 50 milliseconds. Sustained use (4 or more weeks) of taco-shaped lateral buttress may reduce the latency period by at least 51 milliseconds.

Lateral foot-ankle buttress 400 is preferably comprised of a semi-rigid material. The type of material may be any thin, resilient material, such as polycarbonate plastic, or any other suitable semi-rigid material. Typically, lateral foot-ankle buttress 400 will have one or more openings configured to enhance the conformability of the lateral buttress to the foot of the user. Advantageously, lateral foot-ankle buttress has at least a first pair of openings 420 disposed between the flared upper portion 405 and the medial portion 410, wherein the pair of openings 420 are divided by a segment 425 of the lateral foot-ankle buttress 400. In one embodiment, the pair of openings 420 are asymmetrical and comprise at least 10% of the total area of lateral foot-ankle buttress 400.

In other embodiments, the pair of openings comprise at least 40% of the total area of lateral foot-ankle buttress 400. More preferably, the lateral foot-ankle buttress 400 also has a second pair of openings 430 disposed between the medial portion 410 and the flared lower portion 415, wherein the second pair of openings 430 are divided by a second segment 435 of the lateral foot ankle buttress 400. In one embodiment, the second pair of openings 430 are asymmetrical and comprise at least 10% of the total area of lateral foot-ankle buttress 400. In an alternate embodiment, the second pair of openings 430 are symmetrical and comprise at least 10% of the total area of lateral foot-ankle buttress 400. In yet another embodiment, the pair of openings 430 comprise at least 40% of the total area of lateral foot-ankle buttress 400.

Figure 9:
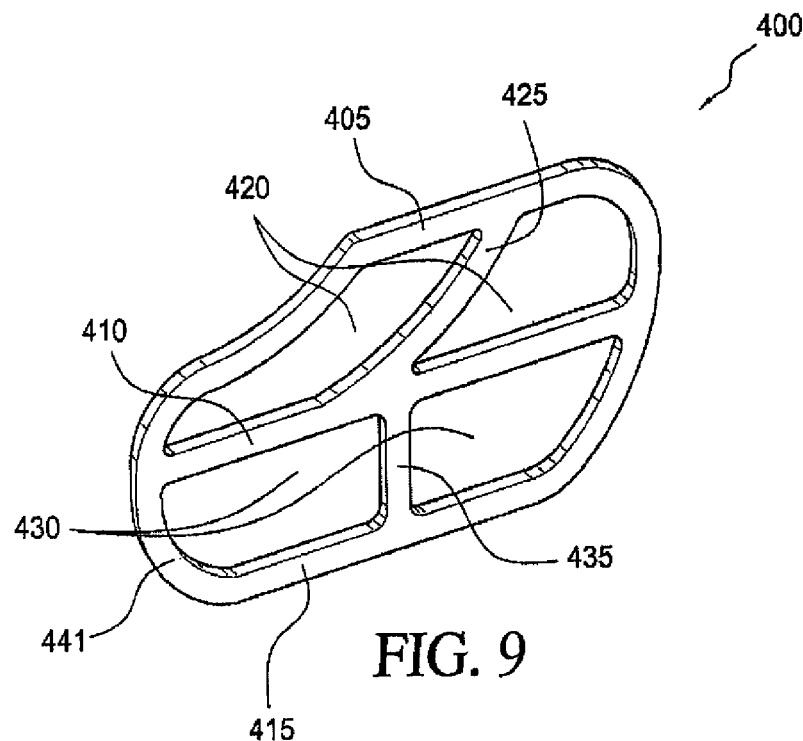
FIG. 9 is a front (anterior) perspective view of a preferred embodiment of the lateral foot-ankle buttress of the present invention.
Figure 10:
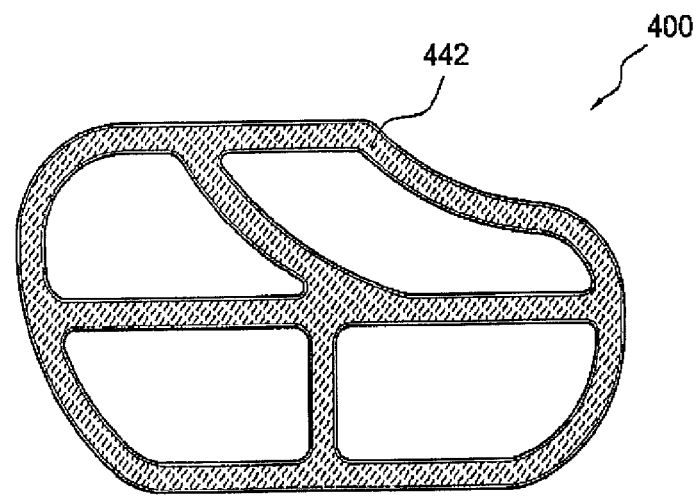
FIG. 10 is a rear (posterior) elevational view of a preferred embodiment of the lateral foot-ankle buttress of the present invention.

Although well designed for use with the topical ankle gear 100 of the present invention, lateral foot-ankle buttress 400 is also highly compatible with other ankle sleeves or topical ankle gear. FIGS. 9-10 depict lateral ankle buttress 400 uncoupled from flexible sleeve 200. As shown in FIG. 10, lateral foot-ankle buttress 400 has a posterior side 441 and an anterior side 442. Anterior side 442 further comprises hook loop fasteners affixed thereto, enabling lateral foot-ankle buttress to releasably couple to flexible sleeve 200 or other ankle gear systems.

FIG. 3 depicts strap 500 designed for use with topical ankle gear 100. Strap 500 may be extendable (stretchable) or inelastic, and with each preferred embodiment comprising a first end 510, a second end 520, and a medial portion 515. Preferably, one or more of first end 510, second end 520, and medial portion 515 further include hook loop fasteners affixed thereto. More preferably, first end 510 and second end 520 have hook loop fasteners. Most preferably, first end 510, second end 520, and medial portion 515 each have hook loop fasteners affixed thereto. First end 510, medial portion 515, and second end 520 of strap 500 can be releasably coupled to flexible sleeve 200 in any user-selected position. In a preferred embodiment (see FIGS. 4-6), strap 500 is arrayed in a "figure eight" configuration and releasably coupled to flexible sleeve 200. In an alternately preferred embodiment (see FIGS. 7-8), strap 500 is arrayed in a "heel-lock" configuration and releasably coupled to flexible sleeve 200. One of ordinary skill in the art would readily understand that the preferred configuration and placement of strap 500 on and around flexible sleeve 200 will vary depending on the needs of the user.

Figure 11:
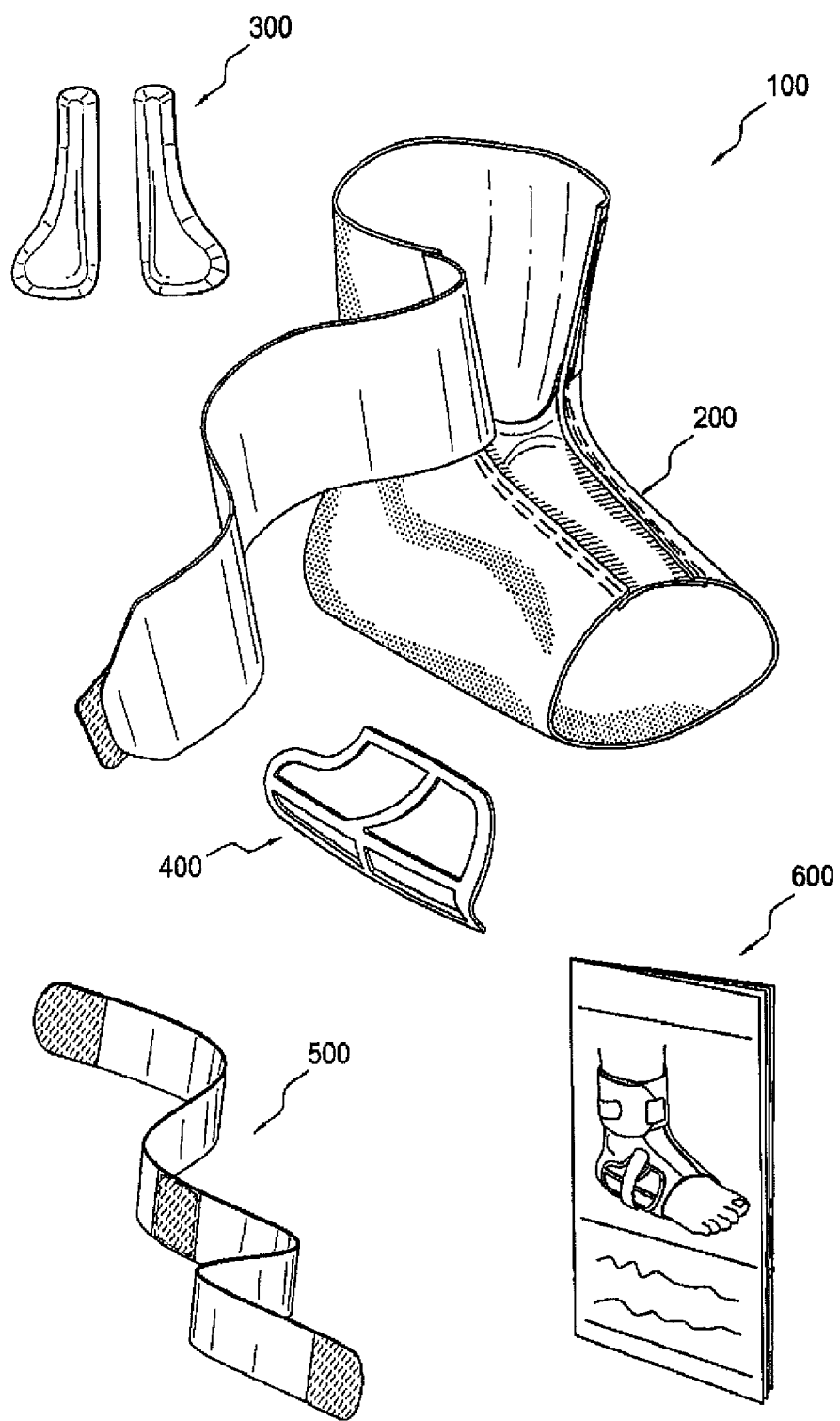
FIG. 11 is a collection of perspective views showing the contents of a preferred embodiment of a kit comprising the present invention.

In another alternate embodiment, topical ankle gear 100 is included in a proprioceptive topical ankle gear kit (see FIG. 11). The kit includes, separately, flexible sleeve 200 (including strap 220), one or more Achilles buttresses 300, lateral foot-ankle buttress 400, and strap 500. Preferably, the kit includes printed instructions 600 relating to the use of the ankle gear, including instructions to couple the lateral foot-ankle buttress 400 to flexible sleeve 200 such that the lateral foot-ankle buttress 400 extends into the ankle-encircling portion 206. More preferably, the printed instructions 600 further include specific directions to couple the first and second Achilles buttresses 300 to the interior surface 203 of flexible sleeve 200 such that the first and second Achilles buttresses 300 are in contact with an Achilles tendon of the user, the first Achilles buttress extending vertically along one side of the Achilles tendon and the second Achilles buttress extending vertically along the other side of the Achilles tendon.

Moreover, upon reading the teachings of this specification, those with ordinary skill in the art will appreciate that, under certain circumstances, considering issues such as changes in technology, user requirements, etc., a variety of fastening devices may be used to "affix", "couple", and/or "releasably couple" (as those words are used herein) one or more components of the present invention. These fastening devices may include one or more of the following: adhesives, bolts, buckles, clasps, latches, locks, screws, snaps, clamps, connectors, couplings, ties, or other fastening means yet to be developed.

The invention is therefore not to be limited to the particular embodiments described and illustrated herein. Although the foregoing describes the preferred embodiments of this invention, it will be understood that the broadest scope of this invention includes modifications. Such scope is limited only by the claims below as read in connection with the above specification. Moreover, many additional advantages of the present invention will be apparent to those skilled in the art in view of the above specification and claims herein.

EXAMPLES

Table 1, below, provides a summary of 6 athletes' experiences wearing a preferred embodiment of the topical ankle gear of the present invention. Before using (or switching to) the topical ankle gear of the present invention, each athlete used a previously available ankle brace (such as the Active Ankle) during volleyball season. There were five female subjects and one male subject. Collectively, the athletes reported no injuries after switching to the topical ankle gear of the present invention. Each athlete preferred the topical ankle gear to his or her previous brace.

TABLE 1

| Subject | Previous Brace & # of Volleyball Games or Seasons Worn | # Volleyball Games (or duration) Worn After Switching to Preferred Embodiment | Adverse Incidents Reported since Initiating Use of Present Invention | Injuries Sustained since Switching to a Preferred Embodiment of the Present Invention | Preferred Device: Previous brace or Preferred Embodiment |
|---|---|---|---|---|---|
| #1 (Female) | Active Ankle 30 games | 105 | 1 (ankle started to invert - no injury sustained) Subject did not sustain injury | None | Preferred Embodiment |
| #2 (Female) | Active Ankle 2 seasons | 70 | None | None | Preferred Embodiment |
| #3 (Female) | Active Ankle 5 Seasons | 40 | None | None | Preferred Embodiment |
| #4 (Female) | Current User | 3 months | None | None | Preferred Embodiment (during strength and conditioning) |

TABLE 1-continued

| Subject | Previous Brace & # of Volleyball Games or Seasons Worn | # Volleyball Games (or duration) Worn After Switching to Preferred Embodiment | Adverse Incidents Reported since Initiating Use of Present Invention | Injuries Sustained since Switching to a Preferred Embodiment of the Present Invention | Preferred Device: Previous brace or Preferred Embodiment |
|---|---|---|---|---|---|
| #5 (Female) | Same as above | Same as above | Same as above | Same as above | Same as above |
| #6 (Male) | Lace-up Ankle Brace 2 weeks | 2 weeks (right foot only) | None | None | Preferred Embodiment |

What is claimed is:

1. Topical ankle gear for enhancing performance and reducing the chance of injury, the ankle gear comprising:
   a flexible sleeve having an interior and an exterior surface, the sleeve comprising a lower leg encircling portion, an ankle encircling portion, and a foot encircling portion; and
   a lateral foot-ankle buttress coupled to the foot encircling portion of the sleeve and extending into the ankle encircling portion, the lateral foot-ankle buttress comprising:
      a flared upper portion having a first region that is configured to extend over and provide resistance to an anterior portion of the foot and a second region that is configured to fit in close proximity to, but under, a user's lateral malleolus;
      a medial portion configured to conform to and extend around a user's foot, while providing resistance to a lateral portion of the foot;
      a flared lower portion configured to extend under and provide resistance to a posterior portion of the foot; and
      at least a pair of openings disposed between the flared upper portion and the medial portion of the lateral foot-ankle buttress, the pair of openings divided by a segment of the lateral foot-ankle buttress extending between the flared upper portion and the medial portion such that the openings are at least 40% of the total area of the lateral foot-ankle buttress.

2. The ankle gear of claim 1, wherein the lateral foot-ankle buttress stimulates sensory and tactile receptors of a user's foot and ankle including the anterior talofibular (ATFL) and calcaneo fibular ligaments when worn.

3. The ankle gear of claim 1, wherein a latency period in a user's muscle spindles is reduced by at least one millisecond when the ankle gear is worn.

4. The ankle gear of claim 1, wherein the flexible sleeve is sufficiently elastic to provide between 15-25 mm Hg compression when worn by the user.

5. The ankle gear of claim 1, wherein the lateral foot-ankle buttress is semi-rigid and releasably coupled to the flexible sleeve.

6. The ankle gear of claim 1, further comprising:
   a first and second Achilles buttress coupled to the interior of the ankle encircling portion of the sleeve and extending vertically thereabove along the interior of the lower leg encircling portion, such that when the ankle gear is worn by a user, the first and second Achilles buttresses are in contact with an Achilles tendon of the user, the first Achilles buttress extending vertically along one side of the Achilles tendon and the second Achilles buttress extending vertically along the other side of the Achilles tendon.

7. The ankle gear of claim 6, wherein the flexible sleeve is radially stretchable and contours to the user's lower leg, ankle and foot, compressing the first and second Achilles buttresses towards the user's Achilles tendon when worn, thereby stimulating the user's sensory and tactile receptors of the foot and ankle.

8. The ankle gear of claim 5, wherein the Achilles buttresses apply pressure to one or more constituents of the peroneal muscle group including the peroneous longus (PL), peroneous brevis (PB), and tibialis anterior (TA) muscle spindles.

9. The ankle gear of claim 1, wherein the flexible sleeve comprises a thickness of less than 2 mm.

10. The ankle gear of claim 6, wherein the first and second Achilles buttresses are releasably coupled to the flexible sleeve and are substantially elliptical.

11. The ankle gear of claim 1, wherein the lower leg encircling portion and least a portion of the ankle encircling portion of the flexible sleeve has at least a 15% reduced diameter compared to the foot encircling portion of the flexible sleeve.

12. Topical ankle gear for enhancing performance and reducing the chance of injury, the ankle gear comprising:
   a flexible sleeve having an interior and an exterior surface, the sleeve comprising a lower leg encircling portion, an ankle encircling portion, and a foot encircling portion;
   a first and second Achilles buttress coupled to the interior of the ankle encircling portion of the sleeve and extending vertically thereabove along the interior of the lower leg encircling portion, such that when the ankle gear is worn by a user, the first and second Achilles buttresses are in contact with an Achilles tendon of the user, the first Achilles buttress extending vertically along one side of the Achilles tendon and the second Achilles buttress extending vertically along the other side of the Achilles tendon; and
   a lateral foot-ankle buttress coupled to the foot encircling portion of the sleeve and extending into the ankle encircling portion, the lateral foot-ankle buttress comprising a flared upper portion having a first region that is configured to extend over and provide resistance to an anterior portion of the foot and a second region that is configured to fit in close proximity to, but under a user's lateral malleolus.

13. The ankle gear of claim 12, wherein the lateral foot-ankle buttress increases proprioception in a user, stimulates the stretch reflex, and reduces the latency period in the muscle spindles.

14. The ankle gear of claim 12, wherein at least a portion of the flexible sleeve is breathably configured to release perspiration and allow air flow during use.

15. The ankle gear of claim 12, wherein the lower leg encircling portion of the flexible sleeve further comprises a strap releasably coupled to the flexible sleeve and is configured to extend substantially circumferentially around the flexible sleeve.

16. The ankle gear of claim 12, wherein the lateral foot-ankle buttress further comprises:

a medial portion configured to conform to and extend around a user's foot, while providing resistance to a lateral portion of the foot; and a flared lower portion configured to extend under and provide resistance to a posterior portion of the foot.

17. The ankle gear of claim 12, wherein the Achilles buttresses are comprised of a compressible foam, foam-like, gel, or gel-like material.

18. The ankle gear of claim 12, further comprising an extendable strap with a first end and a second end, wherein the first end is coupled to the foot encircling portion, the strap extending therefrom over and in contact with the flared upper portion of the lateral foot-ankle buttress, wrapping substantially circumferentially around the ankle encircling portion or foot encircling portion, and coupling to the leg encircling portion at the second end.

* * * * *